United States Patent [19]
Lahm et al.

[11] Patent Number: 5,795,775
[45] Date of Patent: Aug. 18, 1998

[54] CULTURE VESSEL AND ASSEMBLY

[75] Inventors: William J. Lahm, Sumter, S.C.;
Timothy A. Stevens, Warwick, N.Y.;
Alexander G. Tschumakow,
Sommerville; Leon M. Wilkins, North
Andover, both of Mass.; **John M.
Janson, Piscataway, N.J.; Stephen C.
Conley**, North Attleboro, Mass.

[73] Assignee: Becton Dickinson and Company,
Franklin Lakes, N.J.

[21] Appl. No.: 721,393

[22] Filed: Sep. 26, 1996

[51] Int. Cl.⁶ .................................................. C12M 3/06
[52] U.S. Cl. .................................. 435/297.5; 435/305.1;
435/305.2; 435/305.3; 435/305.4; 435/297.1
[58] Field of Search .......................... 435/288.3, 288.4,
435/297.1, 297.5, 305.1–305.4

[56] References Cited

U.S. PATENT DOCUMENTS

| | | | |
|---|---|---|---|
| 5,026,649 | 6/1991 | Lyman et al. | 435/297.5 |
| 5,358,871 | 10/1994 | Stevens et al. | 435/305.2 |
| 5,366,893 | 11/1994 | Stevens et al. | 435/305.2 |
| 5,468,638 | 11/1995 | Barker et al. | 435/305.1 |
| 5,534,227 | 7/1996 | Lahm et al. | 435/297.5 |

*Primary Examiner*—William H. Beisner
*Attorney, Agent, or Firm*—Nanette S. Thomas; Bruce S. Weintraub

[57] ABSTRACT

An assembly and components therefor are disclosed for use in the field of cell and tissue culture. The assembly includes a base having one or more wells, and a cell culture insert which is mountable to the base such that the bottom wall of the insert is suspended within the well. Each well has a generally rectangular configuration such that openings are provided at each corner of the well for introducing fluid to the well. A cover is provided for protecting the assembly and maintaining the position of the cell culture insert.

13 Claims, 7 Drawing Sheets

5,795,775

1

CULTURE VESSEL AND ASSEMBLY

BACKGROUND OF THE INVENTION

1. Field of the Invention

The invention relates to a vessel and an assembly for growing cells or tissue culture in vitro, and more particularly to a vessel and an assembly wherein cells or other biological materials can be suspended within a nutrient medium.

2. Description of the Related Art

Assemblies of various types have been developed for culturing cells. Such assemblies often include a base defining one or more wells, a cell culture insert removably positioned in a well, and a cover mounted to the base for partially or completely covering the well(s). U.S. Pat. Nos. 4,686,190, 4,871,674, 5,026,649, 5,358,871 and 5,366,893 disclose various assemblies for culturing cells. All of these patented assemblies employ a cell culture insert having a permeable bottom which is suspended within a well by a flange extending peripherally from the top portion of the insert. Other types of inserts include legs which support the insert on the bottom surface of the well such that the permeable bottom of the insert is suspended above the bottom surface.

Most of the prior art assemblies disclosed in the above-referenced patents include generally cylindrical wells and generally cylindrical or frustoconical inserts positioned within the wells. Access to the wells using a pipette or the like may accordingly be relatively difficult. In some of the prior art assemblies, pipette openings are provided in the side walls of the inserts. The size of such openings is limited by the size of the inserts. In other assemblies, limited space is provided between the insert and the side wall of the well. The insert must often be displaced or entirely removed in order to gain access to the well.

The assemblies disclosed above also are not optimally designed for all types of tissue cultures. Some procedures involve growing relatively large tissue masses. Some require access to a well by an instrument considerably larger than a pipette. Standard cluster dishes and cell culture inserts are not specifically designed for such applications.

SUMMARY OF THE INVENTION

It is an object of the invention to provide an assembly to be used for cell or tissue culture. The assembly according to the invention includes a base which defines a well, and a cell culture insert which is removably positioned within the well. The well includes an upper opening having a plurality of corner portions. Access to the well is provided through one or more of the corner portions of the well opening when the cell culture insert is positioned within the well.

In accordance with a preferred embodiment of the invention, the well includes two pairs of opposing, generally parallel walls defining four corner portions. The cell culture insert is positioned within the well such that an opening is defined between the top portion of the insert and at least one of the corner portions. The opening provides access to the bottom of the well. Access openings are preferably provided at all four corner portions of the well.

The cell culture insert according to the invention preferably includes two pairs of generally parallel side walls, and a generally rectangular, permeable membrane defining the bottom wall thereof. A rim extends from the side walls for suspending the insert within a well of a base. The rim preferably extends from the top of the side walls, and may be annular.

2

A base for supporting a cell culture insert is also provided by the invention. The base includes one or more wells, each well including two pairs of opposing side walls and a bottom wall. Protrusions extend inwardly from the side walls. Each protrusion includes a step for supporting the rim of a cell culture insert. Discrete projections may extend upwardly from the bottom wall of the base. The projections are substantially shorter in height than the side walls.

DETAILED DESCRIPTION OF THE INVENTION

Figure 1:
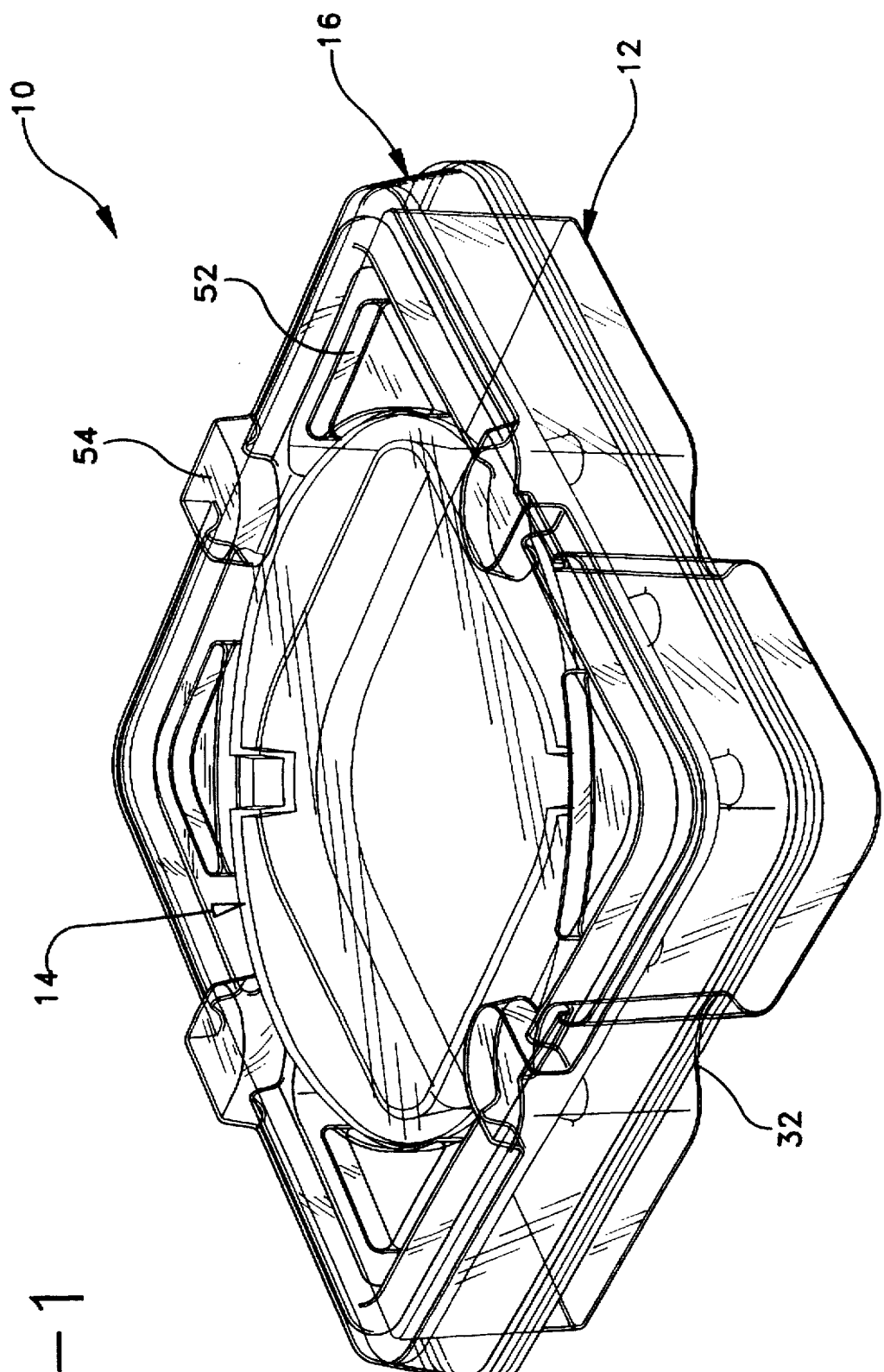
FIG. 1 is a top perspective view of a cell culture assembly according to the invention, including a cover.
Figure 2:
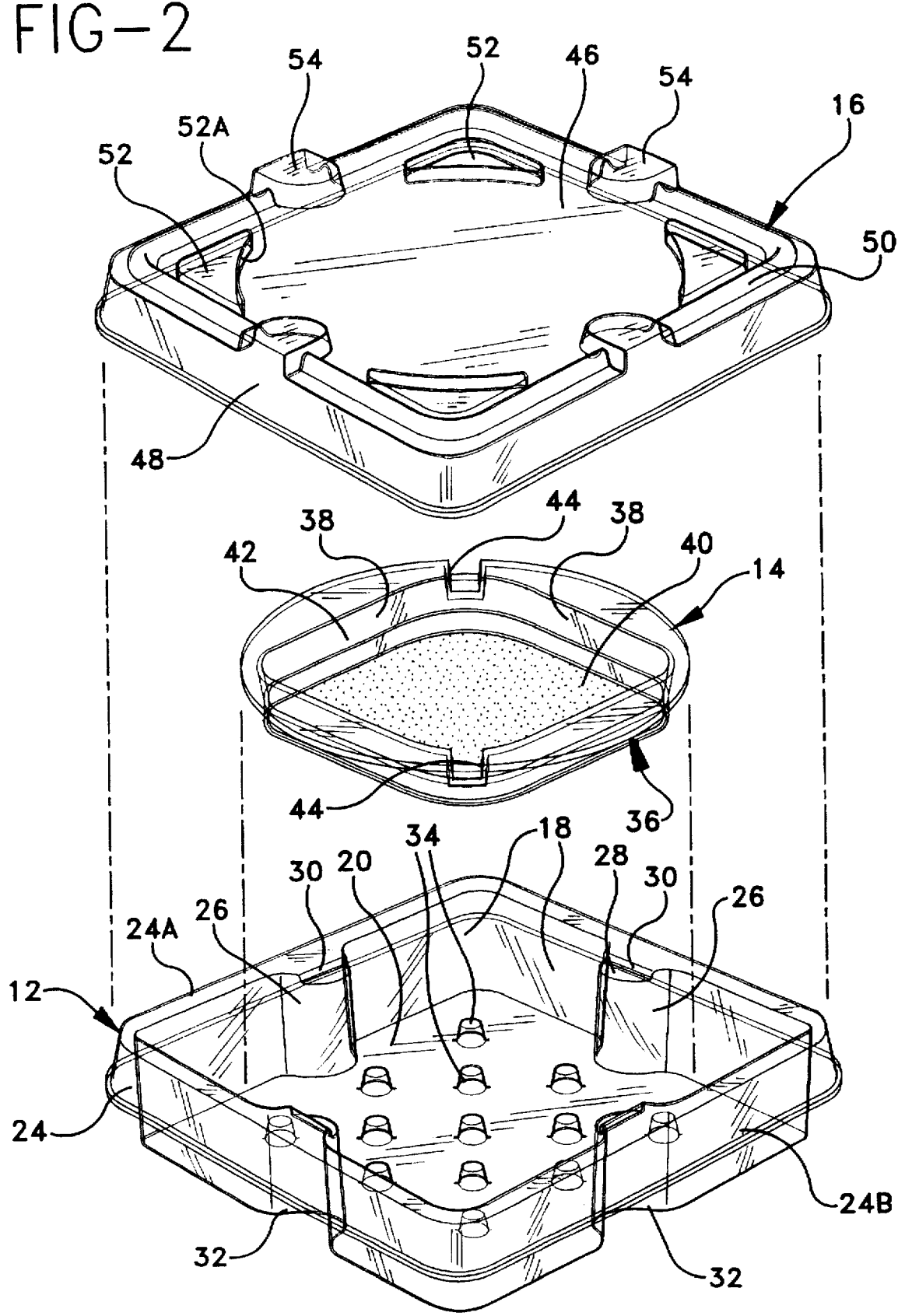
FIG. 2 is an exploded, top perspective view thereof.
Figure 7:
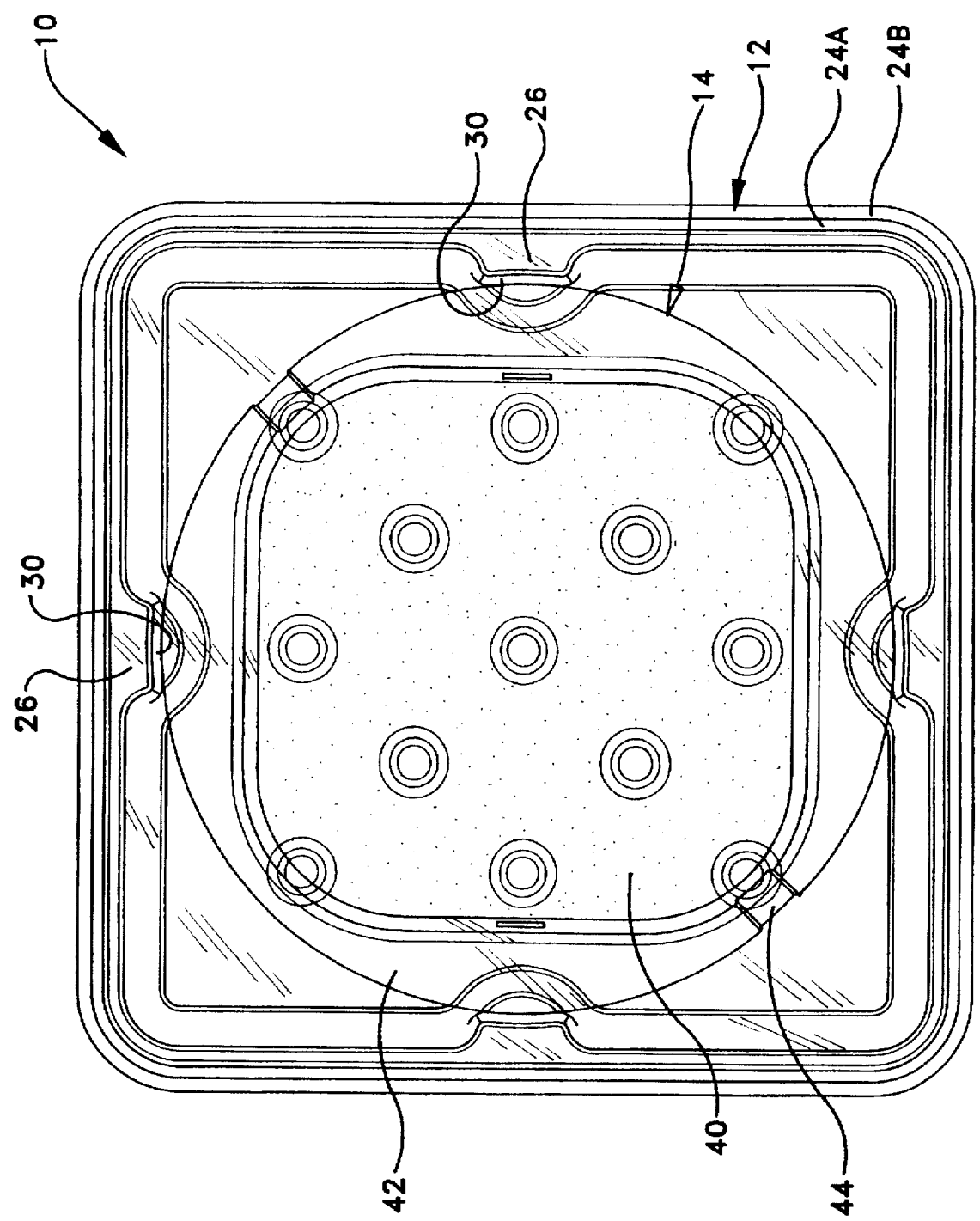
FIG. 7 is a top plan view of the assembly without a cover.

A cell culture assembly 10 according to the invention is shown in FIGS. 1, 2 and 7. The assembly includes a base 12 and a cell culture insert 14, as best shown in FIG. 2. A cover 16 fits over the base and insert.

The parts of the assembly are preferably thermoformed or molded from a transparent, plastic material such as polystyrene or PETG. This allows all portions of the assembly to be easily viewed, even when the cover is employed.

Figure 3:
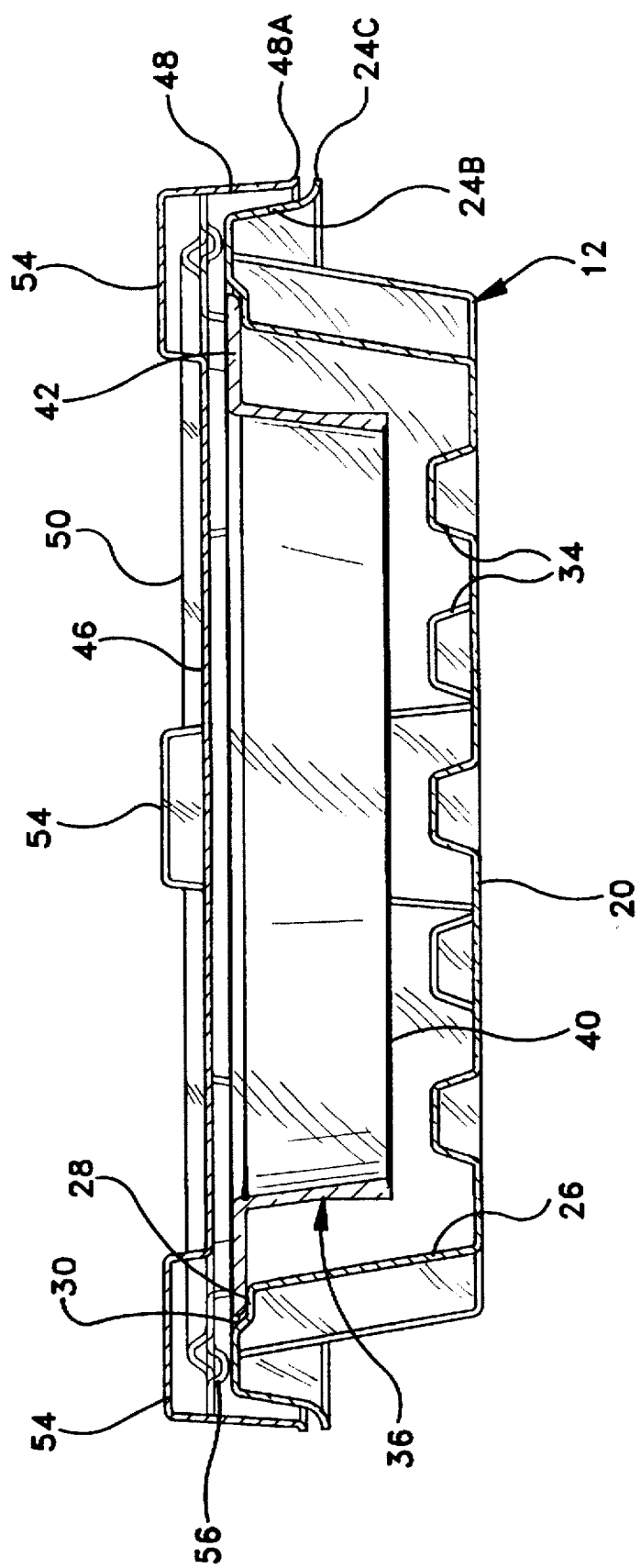
FIG. 3 is a sectional view thereof.
Figure 4:
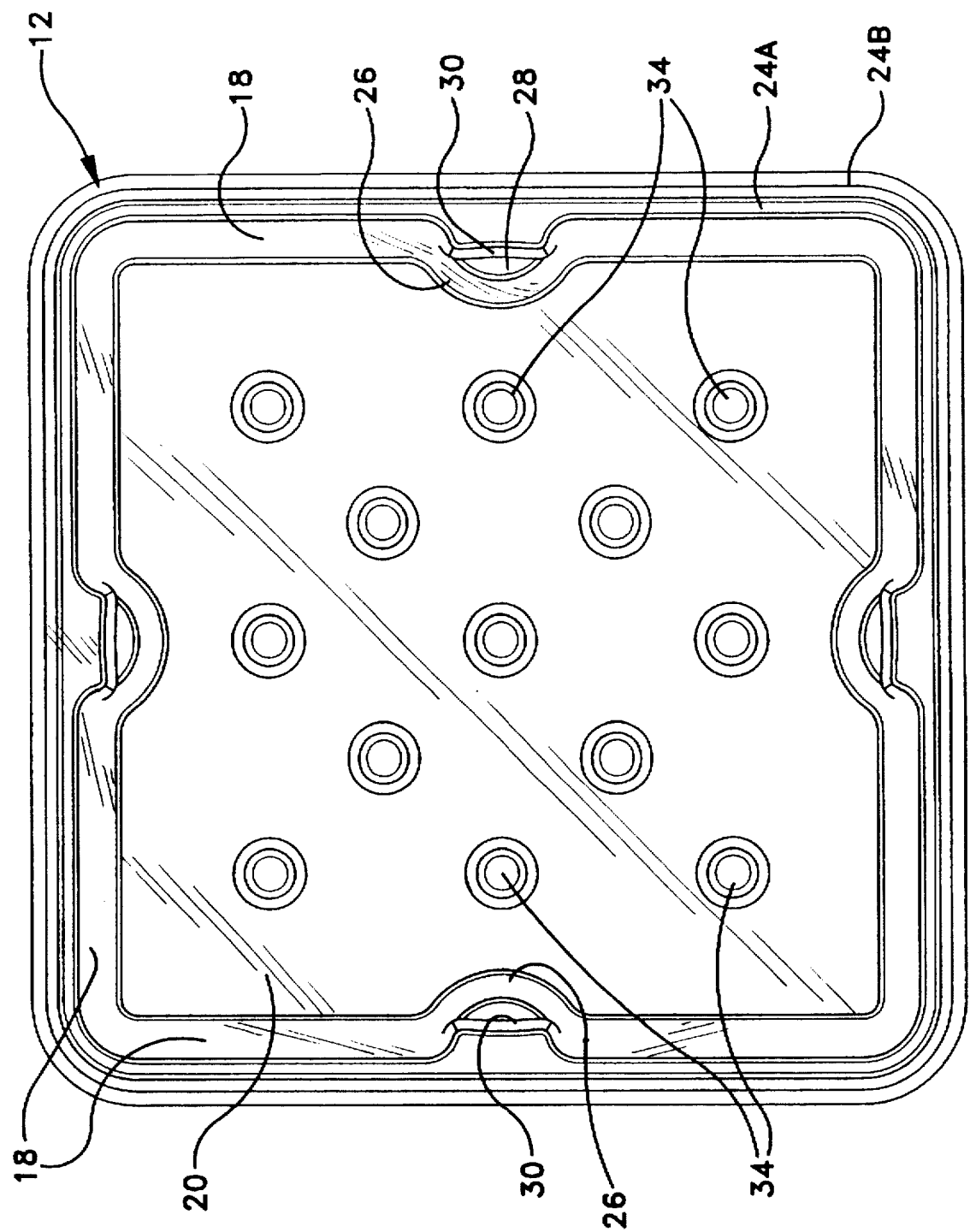
FIG. 4 is a top plan view of the base thereof.
Figure 5:
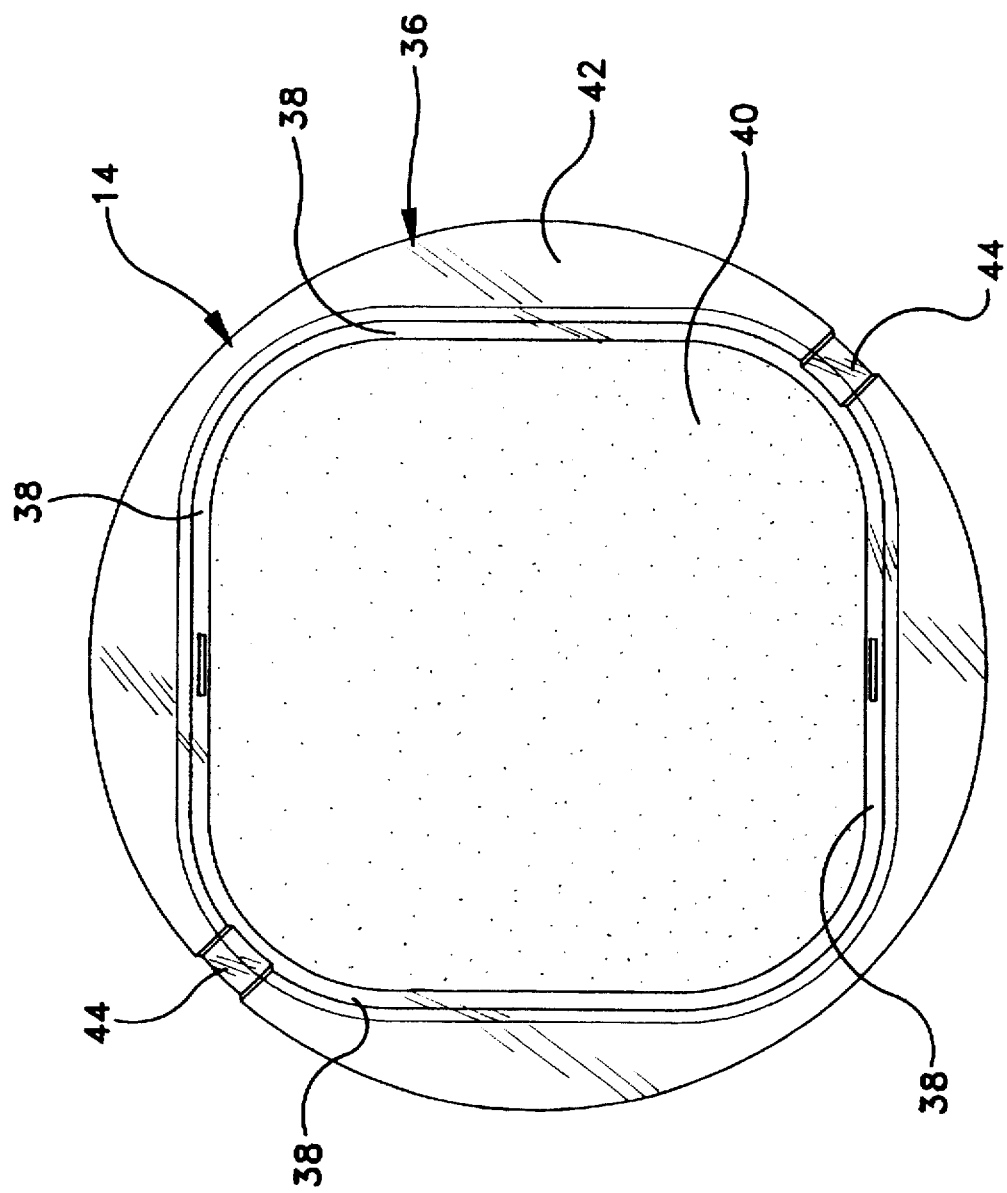
FIG. 5 is a top plan view of the cell culture insert thereof.

The base 12 of the assembly is most clearly shown in FIGS. 2, 3 and 4. The base includes two pairs of opposing, generally parallel side walls 18, a bottom wall 20, and a peripheral flange 24 including a horizontal portion 24A and a downwardly extending portion 24B in opposing relation to the side walls 18.

The side walls 18 define a substantially rectangular opening at the top end of the base. In the preferred embodiment of the invention, the side walls are equal in length, and accordingly define a substantially square opening. The side walls adjoin each other at rounded corners.

The dimensions of the bottom wall 20 are slightly smaller than those of the top opening as the side walls 18 taper inwardly from top to bottom. The bottom and side walls define a well which is capable of retaining a liquid or solid medium.

Each side wall includes a protrusion 26 in the form of a rounded column extending within the well. The protrusions are located substantially at the midpoint of each side wall. Each protrusion is accordingly positioned in opposing relation to the protrusion extending from the opposing side wall.

A step including a horizontal surface 28 and a vertical surface 30 is formed at the top of each protrusion 26. The vertical surface 30 extends substantially parallel to the side wall from which the protrusion extends.

Each protrusion 26 includes a rounded inner surface extending between the bottom wall 20 and the top of the base. The outer surface of each protrusion forms a corresponding rounded, elongate depression within the outer surface of each side wall. The depressions 32 and flange 24 facilitate handling of the base 12.

A plurality of discrete, frustoconical projections 34 extend upwardly from the bottom wall 20 of the base. The projections are all substantially the same height, and are substantially shorter than the height of the side walls 18. The configurations and locations of the projections may be varied if desired. It is important that the projections allow a liquid introduced into the well to spread over the entire bottom surface of the well. In other words, the projections should not be connected in such a manner that they would prevent liquid from passing into any otherwise open space at the bottom of the well.

The cell culture insert 14 includes a body 36 having two pairs of opposing side walls 38. A permeable membrane 40 is secured to the bottom end of the body. The membrane may be made from any material suitable for growing or maintaining the particular cells or tissues deposited thereon. A variety of membranes are commercially available, some of which are more suitable for certain procedures than for others. U.S. Pat. No. 5,366,893, the disclosure of which is incorporated by reference, discloses several membrane materials. Polycarbonate micropore filters, for example, have been used for cell cultures including endothelial cells.

The side walls of the cell culture insert, being substantially equal in length, define substantially rectangular openings at the top and bottom ends thereof. The membrane 40 is accordingly substantially rectangular.

A substantially annular rim 42 extends outwardly from the top end of the body 36. The diameter of the rim is slightly less than the distance between the opposing vertical surfaces 30 of each pair of opposing protrusions 26. The rim accordingly rests upon the horizontal surfaces 28 of the respective steps when the insert is mounted to the base. The edge of the rim adjoins the vertical surfaces 30 of each step. The insert is accordingly maintained in place by the steps, with the membrane 40 positioned slightly above the upper surfaces of the projections 34. While the insert could be supported by legs engaging the bottom wall of the well, as disclosed in U.S. Pat. No. 5,366,823, the use of a rim extending from the insert body is preferred. The thickness of the rim is approximately the same as the height of the vertical surface 30 of each step. The top surface of the rim is accordingly substantially coplanar with the top surface of the base.

A pair of notches 44 extend through the side walls and rim of the insert at diagonally opposing corner portions of the side walls. Each notch includes a bottom wall and a pair of opposing side walls, all extending below the rim.

The size of the insert is selected in accordance with the particular test or other procedure to be conducted. In a preferred embodiment according to the invention, the maximum diameter of the insert 14 is about one hundred fifty millimeters. The height is about twenty-four millimeters. By providing a diameter at least three times the height of the insert, a relatively shallow pan is provided, which facilitates certain test procedures.

Figure 6:
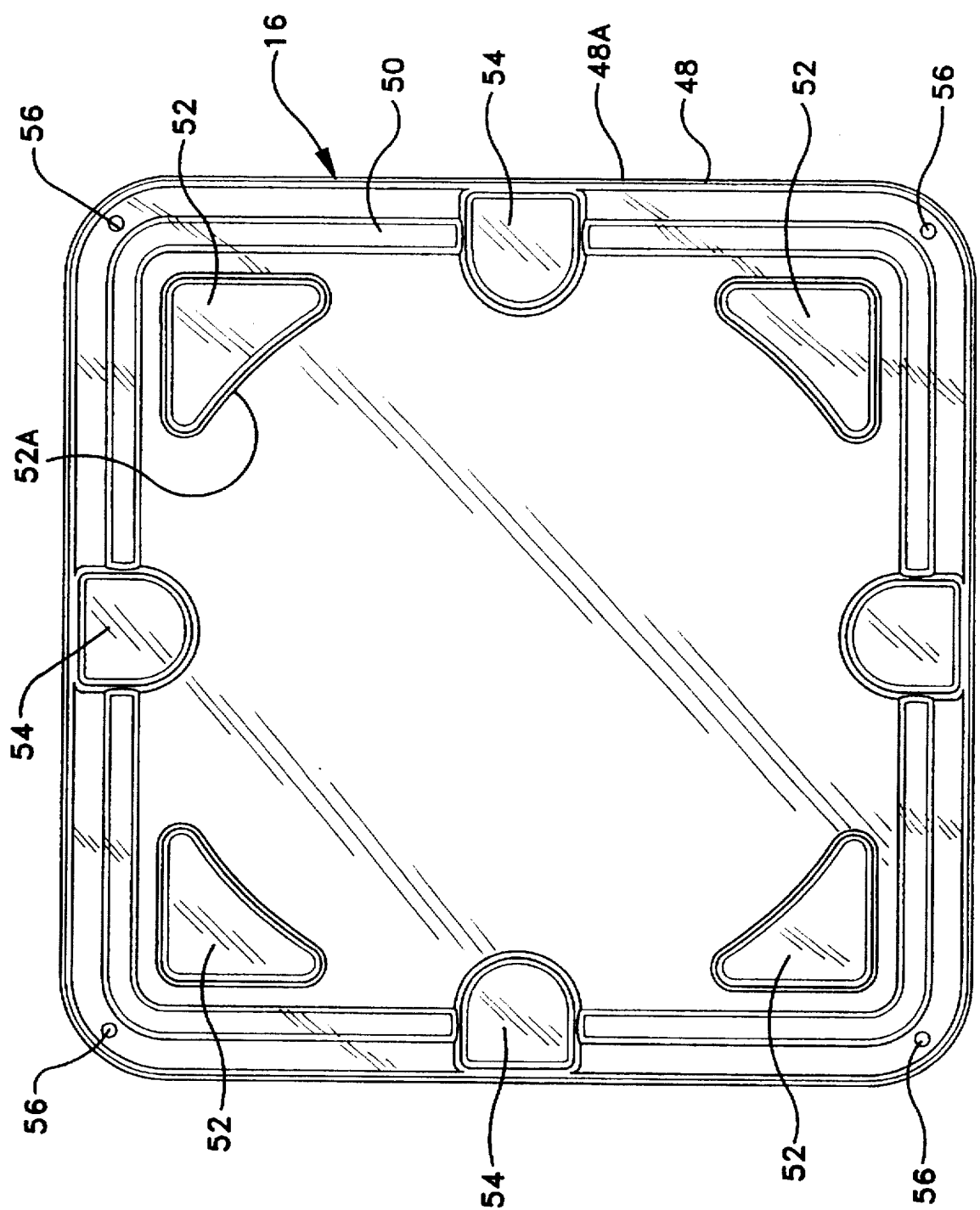
FIG. 6 is a bottom plan view of the cover thereof.

The cover 16 is designed to fit over the base and insert. Referring to FIGS. 2 and 6, the cover includes a top wall 46 and a downwardly extending flange 48. As shown in FIG. 6, a peripheral ridge 50 is formed in the top wall 46. The ridge extends above the plane of the center portion of the top wall. Each corner portion of the top wall includes a generally triangular depression 52 having an arcuate inner edge 52A. These depressions assist to hold the insert in place during shipment to assure integrity of the insert. Two pairs of opposing protrusions 54, each having arcuate inner edges, extend above the plane of the top wall. Each protrusion 54 is located mid-way between each corner portion of the cover 16. Four small circular depressions 56 are formed at the respective corners of the cover, just outside the ridge 50.

When the cover 16 is mounted to the base 12, the small, circular depressions 56 rest upon the horizontal portion 24A of the peripheral flange 24 of the base. This arrangement facilitates removal of the cover which, in the absence of such depressions, would be more likely to stick to the base. The opposing pairs of protrusions 54 of the cover are positioned directly over the column-like protrusions 26 of the base. The triangular depressions 52 extend into the well such that the arcuate inner edges thereof adjoin the outer edge of the rim 42 of the cell culture insert 14. The cover accordingly prevents lateral or vertical displacement of the insert 14 with respect to the base. The ridge and depressions also make the covered assembly relatively easy to handle.

The flange 48 of the cover extends over the downwardly extending portion 24B of the flange 24 of the base 12. Each flange 48, 24 includes a small, outwardly extending lip designated by numerals 48A and 24C, respectively. The lips 48A, 24C are separated by a small space when the cover is applied, as shown in FIG. 3.

In use, the well defined by the base 12 may be partially filled with a selected medium. This may be accomplished with the insert in place through the generally triangular openings defined between the rim 42 and the corner portions of the base. Tissues or cells may be deposited on the top side of the membrane. The insert 14 may be rotated into a position where the side walls of the insert are parallel to the side walls of the base. The notches 44 facilitate manipulation of the insert within the well.

While shown as a single well assembly 10, the principles of the invention can be applied to a multi-well assembly. By providing wells having non-circular top openings including one or more corner portions, a relatively large opening or openings can be provided between a base and the outer edges of a cell culture insert. Square well openings provide an efficient design for both single and multi-well applications.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An assembly for growing cells or tissue cultures, comprising:

a base defining a well bounded by a bottom wall and a plurality of side walls, said side walls defining a well opening including a plurality of corner portions, and further including a plurality of discrete projections extending upwardly from said bottom wall of said well;

a cell culture insert removably mountable to said base, said cell culture insert including a substantially rectangular permeable membrane, a hollow body having a bottom end to which said permeable membrane is affixed and a top portion defining an open end providing access to said permeable membrane, said body being positionable within said well such that said permeable membrane is positioned above said bottom wall of said well above said discrete projections, and further wherein said body of said cell culture insert includes two pairs of opposing, substantially straight side walls, each of said side walls including substantially coplanar top ends and substantially coplanar bottom ends, and further wherein said side walls define two pairs of diagonally opposing corner portions, and a pair of notches defined within the top ends of said side walls at diagonally opposing corner portions, and an opening defined between said top portion of said body and at least one of said corner portions of said well opening when said cell culture insert is mounted to said base, said opening providing access to said bottom wall of said well.

2. An assembly as described in claim 1 including a rim extending outwardly from said top portion of said cell culture insert, said rim being supportable by said base.

3. An assembly as described in claim 2 including a plurality of protrusions extending inwardly from said side walls of said base, said rim being supportable by said protrusions.

4. An assembly as described in claim 3 wherein said base includes two pairs of opposing side walls defining a substantially rectangular well opening, and each of said inwardly extending protrusions includes a step defined by a horizontal surface and a vertical surface, said rim being supportable by said horizontal surfaces of said steps in adjoining relation to the vertical surfaces of said steps.

5. An assembly as described in claim 4, wherein said top portion of said body of said cell culture insert includes a first notch of said pair of notches extending therein for facilitating positioning said body with respect to said base, and a second notch of said pair of notches extending therein, said second notch being in opposing relation to said first notch.

6. An assembly as described in claim 2 including a cover supported by said base, said cover including a plurality of depressions extending within said well and adjoining said rim of said cell culture insert when said cell culture insert is mounted to said base.

7. An assembly as described in claim 2, wherein said rim is generally annular.

8. An assembly as described in claim 1, wherein openings are defined between said top portion of said body and each of said corner portions of said well opening when said cell culture insert is mounted to said base.

9. An assembly as described in claim 1, wherein said body of said cell culture insert and said well are both substantially square in configuration.

10. An assembly as described in claim 1, wherein the diameter of said cell culture insert is at least three times greater than the height thereof.

11. A cell culture insert for growing cells or tissue cultures, comprising:

a hollow body including two pairs of opposing, substantially straight side walls, each of said side walls including substantially coplanar top ends and substantially coplanar bottom ends;

a generally rectangular, permeable membrane secured to said bottom ends of said side walls, and a flange extending outwardly from said top ends of said walls, wherein said side walls define two pairs of diagonally opposing corner portions, and a pair of notches defined within the top ends of said side walls at diagonally opposing corner portions.

12. A cell culture insert as described in claim 11, wherein said flange is generally annular.

13. A cell culture insert as described in claim 12, wherein said permeable membrane has a substantially square, planar configuration.

* * * * *

UNITED STATES PATENT AND TRADEMARK OFFICE
CERTIFICATE OF CORRECTION

PATENT NO. : 5,795,775
DATED : August 18, 1998
INVENTOR(S) : WILLIAM J. LAHM ET AL.

It is certified that error appears in the above-identified patent and that said Letters Patent are hereby corrected as shown below:

On the Title Page item [73], after "N.J." insert --; and Organogenesis, Inc., Canton, Mass.--.

Signed and Sealed this

Twenty-third Day of May, 2000

Attest:

Q. TODD DICKINSON

Attesting Officer

Director of Patents and Trademarks